US011419576B2

United States Patent
Sakaguchi et al.

(10) Patent No.: US 11,419,576 B2
(45) Date of Patent: Aug. 23, 2022

(54) MEDICAL DEVICE

(71) Applicant: TERUMO KABUSHIKI KAISHA, Tokyo (JP)

(72) Inventors: Yuuki Sakaguchi, Fujinomiya (JP); Yasunori Yamashita, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 451 days.

(21) Appl. No.: 15/673,607

(22) Filed: Aug. 10, 2017

(65) Prior Publication Data
US 2018/0055480 A1   Mar. 1, 2018

(30) Foreign Application Priority Data

Aug. 31, 2016 (JP) .............................. JP2016-170153

(51) Int. Cl.
| | | |
|---|---|---|
| A61B 8/00 | (2006.01) | |
| A61B 5/00 | (2006.01) | |
| A61B 8/12 | (2006.01) | |
| A61B 6/00 | (2006.01) | |

(52) U.S. Cl.
CPC .......... *A61B 8/4209* (2013.01); *A61B 5/0066* (2013.01); *A61B 5/0084* (2013.01); *A61B 6/4417* (2013.01); *A61B 6/4441* (2013.01); *A61B 8/12* (2013.01)

(58) Field of Classification Search
CPC ... A61B 8/4209; A61B 5/0066; A61B 5/0084; A61B 8/12; A61B 6/4441; A61B 6/4417; A61B 1/00149; A61B 1/00147; A61B 1/0016; A61B 1/0051; A61B 90/50; A61B 1/005; A61B 1/0055; A61B 2090/031; A61B 34/30; A61B 34/304; A61M 25/0161
See application file for complete search history.

(56) References Cited

U.S. PATENT DOCUMENTS

| | | | | |
|---|---|---|---|---|
| 5,596,991 | A  * | 1/1997 | Tanaka ..................... | A61B 8/12 600/459 |
| 6,245,028 | B1 * | 6/2001 | Furst .................. | A61B 10/0233 600/411 |
| 6,292,681 | B1 * | 9/2001 | Moore ..................... | A61B 8/12 600/407 |
| 8,774,901 | B2 * | 7/2014 | Velusamy .............. | A61B 6/032 600/427 |
| 2002/0095175 | A1 * | 7/2002 | Brock .................... | A61B 34/20 606/205 |
| 2002/0195132 | A1 * | 12/2002 | Owczarz .................. | F16F 1/38 134/140 |

(Continued)

FOREIGN PATENT DOCUMENTS

JP           2015-119994 A      7/2015

*Primary Examiner* — Ashley K Buran
*Assistant Examiner* — Amy J Shafqat
(74) *Attorney, Agent, or Firm* — Buchanan Ingersoll & Rooney PC

(57) ABSTRACT

A medical device is disclosed, which includes a motor drive device that is connected to a proximal end of an image diagnosis catheter, and that rotates a drive shaft included in the image diagnosis catheter around an axial direction and moves the drive shaft along the axial direction, and a support unit that supports the motor drive device in a state where the motor drive device is separated in a vertical direction from a laying table on which a subject P is laid.

19 Claims, 8 Drawing Sheets

(56) References Cited

U.S. PATENT DOCUMENTS

| | | | |
|---|---|---|---|
| 2003/0057909 A1* | 3/2003 | Tsukui | G01P 1/08 318/566 |
| 2007/0197939 A1* | 8/2007 | Wallace | A61B 5/6885 600/587 |
| 2013/0188855 A1* | 7/2013 | Desjardins | A61B 5/0033 382/131 |
| 2013/0215249 A1* | 8/2013 | Papalazarou | A61B 6/02 348/77 |
| 2013/0231678 A1* | 9/2013 | Wenderow | A61B 34/30 606/130 |
| 2014/0039314 A1* | 2/2014 | Stoianovici | A61B 8/0841 600/439 |
| 2014/0058406 A1* | 2/2014 | Tsekos | A61B 34/30 606/130 |
| 2017/0348060 A1* | 12/2017 | Blacker | A61M 25/0113 |

* cited by examiner

MEDICAL DEVICE

CROSS-REFERENCES TO RELATED APPLICATIONS

This application claims priority to Japanese Patent Application No. 2016-170153 filed on Aug. 31, 2016, the entire content of which is incorporated herein by reference.

TECHNICAL FIELD

The present disclosure relates to a medical device.

BACKGROUND ART

In the related art, as a medical device used in acquiring a diagnostic image for diagnosing an affected site inside a living body, an image diagnosis catheter is known which is used for an image diagnosis device using intra vascular ultra sound (IVUS) and optical coherence tomography (OCT).

The image diagnosis catheter includes a drive shaft provided with a transmitting and receiving unit for transmitting and receiving an examination wave, and a sheath to which the drive shaft is inserted so as to be movable forward and backward. When in use, the image diagnosis catheter is moved backward, while the drive shaft is rotated by a motor drive device connected to a proximal end of the image diagnosis catheter. This operation enables a so-called pull-back operation (medium drawing operation) for moving the drive shaft from a distal side to a proximal side and a pushing operation for pushing the drive shaft toward the distal side (refer to JP-A-2015-119994).

SUMMARY

When the image diagnosis catheter is used, a subject generally receives treatment in a state where the subject is laid on a bed (also called a laying table). Then, the above-described motor drive device is placed on the laying table in some cases. In order to help prevent interference with a C-arm of an X-ray imaging apparatus, the laying table can have a shape having a width allowing a small margin from a body width of the subject. Therefore, a space where the motor drive device is placed is limited to a lateral position of legs of the subject or a position between both the legs on the laying table.

The present disclosure is made in view of the above-described circumstances, and provides a medical device which can more freely design a position for placing a motor drive device.

In accordance with an exemplary embodiment, a medical device is disclosed, which includes a motor drive device that is connected to a proximal end of an image diagnosis catheter, and that rotates a drive shaft included in the image diagnosis catheter around an axial direction and moves the drive shaft along the axial direction, and a support unit that supports the motor drive device in a state where the motor drive device is separated in a vertical direction from a laying table on which a subject is laid.

According to the medical device configured as described above, the motor drive device is supported by the support unit in a state where the motor drive device is separated from the laying table in the vertical direction. Therefore, it is possible to more freely design a position for placing the motor drive device.

In accordance with an exemplary embodiment, a medical device is disclosed comprising: a motor connected to a proximal end of an image diagnosis catheter, and configured to rotate a drive shaft included in the image diagnosis catheter around an axial direction and move the drive shaft along the axial direction; a support configured to support the motor in a state where the motor is separated in a vertical direction from a laying table on which a subject is laid; and an arch shaped vibration resistance member configured to prevent vibrations generated by the motor, which is disposed on an upper surface of the laying table in an arch shape so as to cross one leg of the subject.

In accordance with an exemplary embodiment, a method of acquiring a diagnostic image, the method comprising: inserting an image diagnosis catheter into a blood vessel of a subject on a laying table; arranging a distal end of the image diagnosis catheter at a target position inside the blood vessel; connecting a motor drive device to a proximal end of the image diagnosis catheter, the motor drive device configured to rotate a drive shaft included in the image diagnosis catheter around an axial direction and move the drive shaft along the axial direction; and arranging a support unit configured to support the motor drive device in a state where the motor drive device is separated in a vertical direction from the laying table on which the subject is laid.

DETAILED DESCRIPTION

Figure 1:
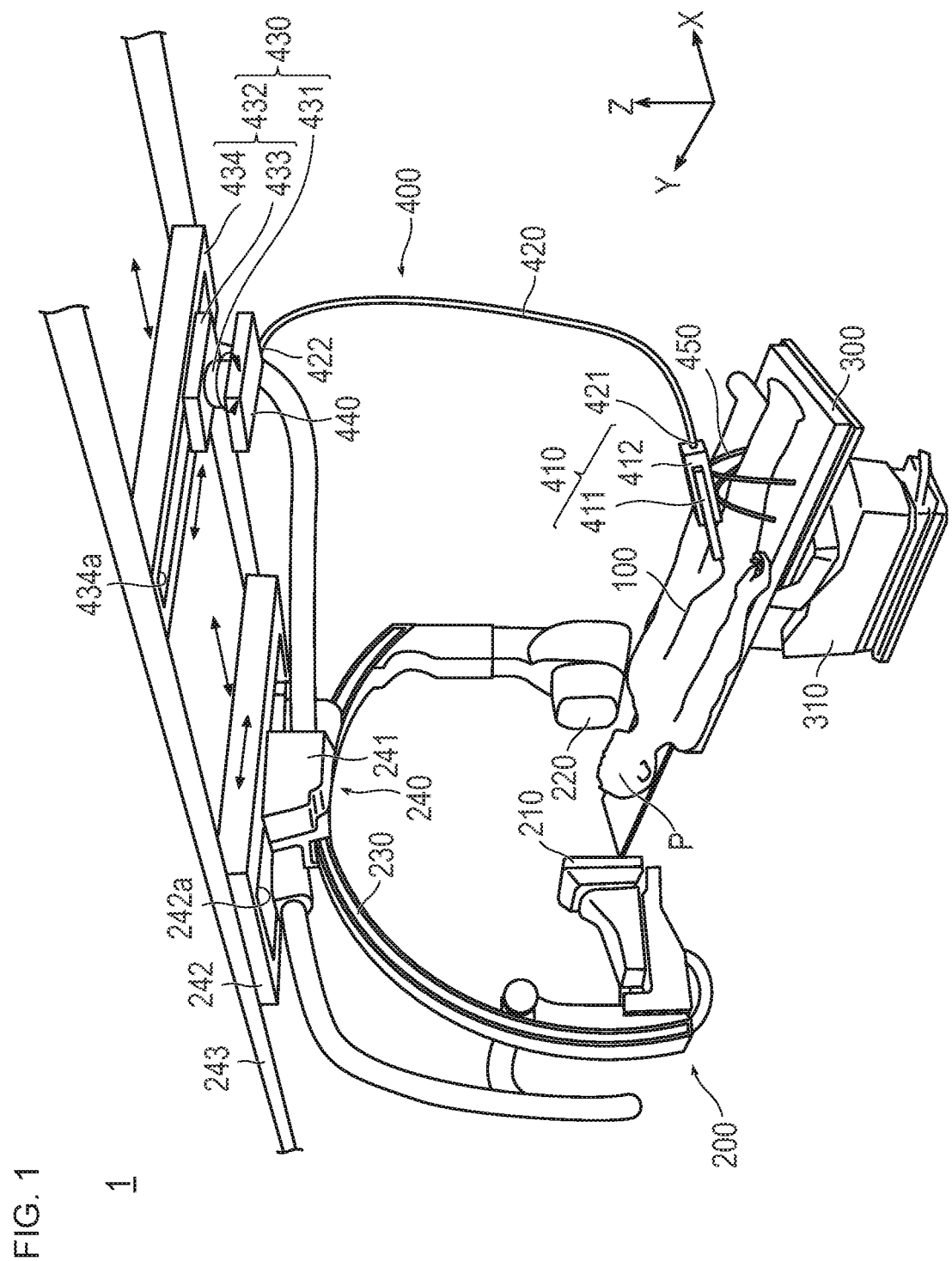
FIG. 1 is a perspective view illustrating a medical system according to a first embodiment of the present disclosure.

Hereinafter, embodiments of the present disclosure will be described with reference to the accompanying drawings. The following description does not limit the technical scope or the meaning of the terms disclosed in claims. In addition, dimensional proportions in the drawings may be exaggerated and different from actual proportions for convenience of description in some cases.

Figure 2A:
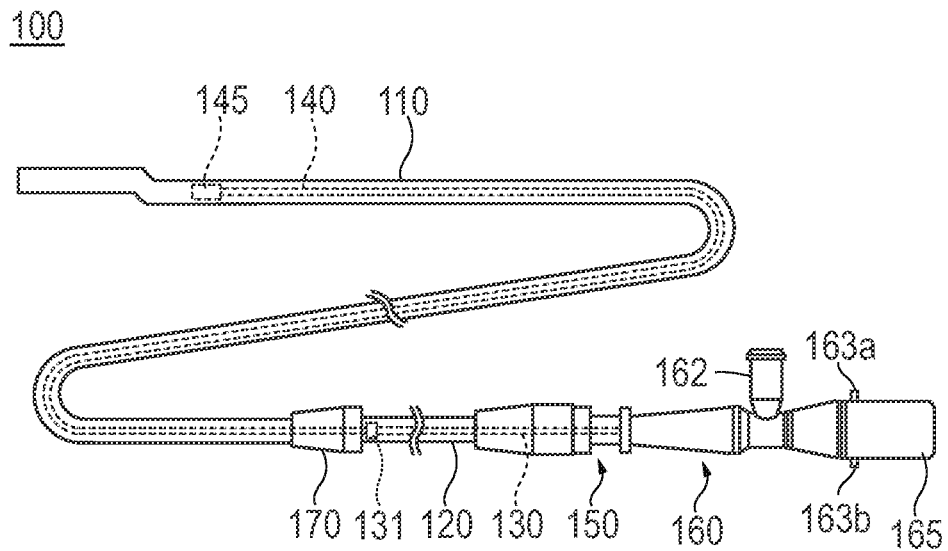
FIG. 2A is a plan view illustrating a state before a pull-back operation is performed of an image diagnosis catheter.
Figure 2B:
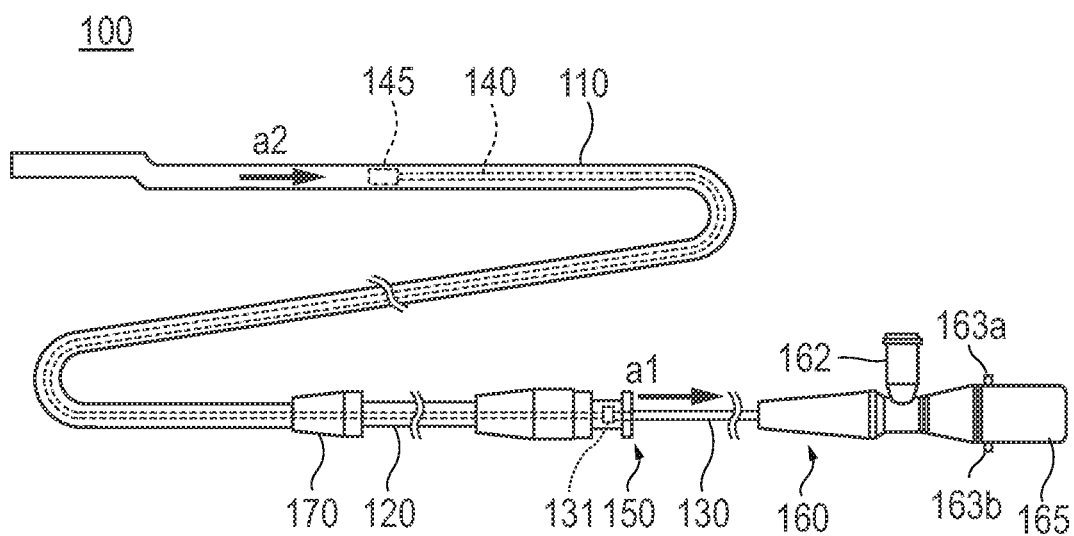
FIG. 2B is a plan view illustrating a state after the pull-back operation is performed of the image diagnosis catheter.
Figure 3:
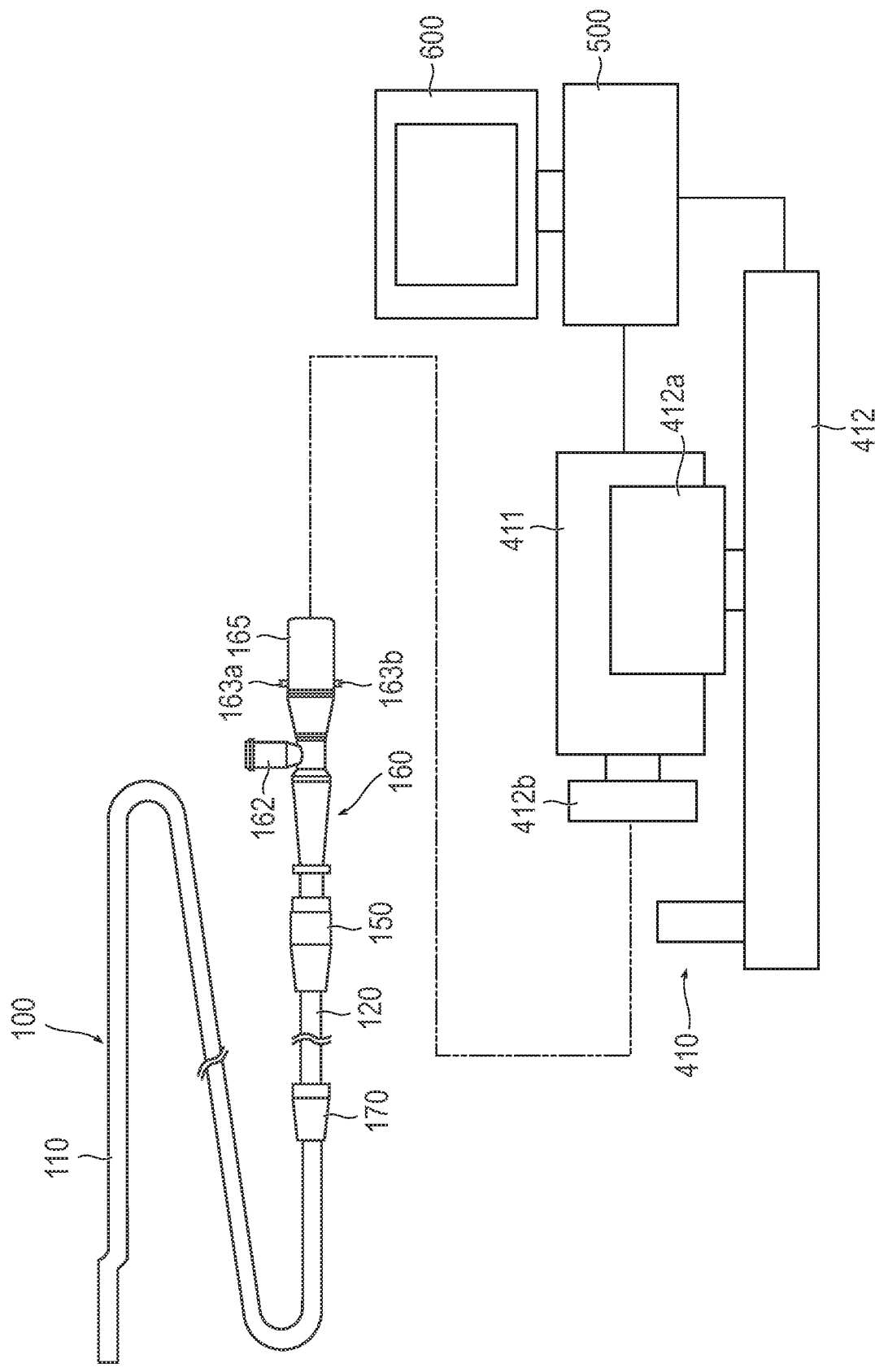
FIG. 3 is a view for describing a configuration of a motor drive device.
Figure 4:
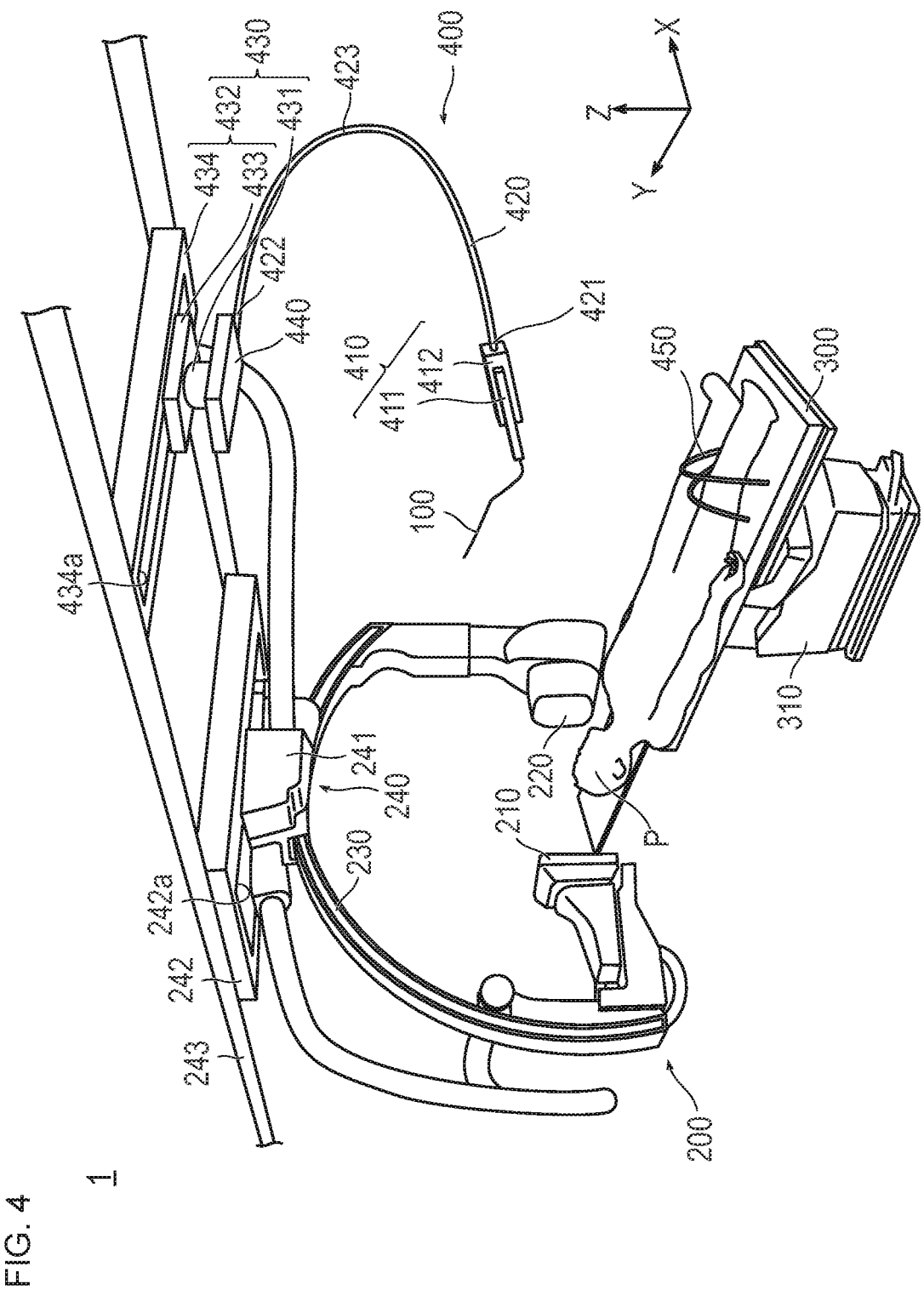
FIG. 4 is a view for describing a method of using the medical system according to the first embodiment.

Hereinafter, a first embodiment according to the present disclosure will be described. FIG. 1 is a perspective view illustrating a medical system 1 according to the first embodiment of the present disclosure. FIGS. 2A and 2B are plan views illustrating a configuration of an image diagnosis catheter 100. FIG. 3 is a view for describing a configuration of a motor drive device 410. FIG. 4 is a view for describing a method of using the medical system 1 according to the first embodiment.

In accordance with an exemplary embodiment, the image diagnosis catheter 100 included in the medical system 1 according to the present embodiment is applicable to intravascular ultra sound (IVUS). As illustrated in FIG. 3, the image diagnosis catheter 100 is driven by being connected to the motor drive device 410. Hereinafter, the medical system 1 will be described with reference to FIGS. 1 to 3.

As illustrated in FIGS. 1 to 3, the medical system 1 has an image diagnosis catheter 100, an X-ray imaging apparatus 200, a laying table 300, a medical device 400, a control unit 500, and a display unit 600. In the following description, an extending direction of a rail unit 243 is referred to as an X-direction, an extending direction of cavity 242a and 434a is referred to as a Y-direction, and a vertical direction is referred to as a Z-direction.

As illustrated in FIG. 1, the image diagnosis catheter 100 is inserted into a body cavity of a living body so as to acquire an image of a lesion area. As illustrated in FIGS. 2A and 2B, the image diagnosis catheter 100 has a sheath 110 inserted into the body cavity of the living body, an outer tube 120 disposed on a proximal side of the sheath 110, an inner shaft 130 inserted into the outer tube 120 so as to be movable forward and backward, a drive shaft 140 which has a vibrator unit 145 for transmitting and receiving a signal in a distal end and which is rotatably disposed inside the sheath 110, a unit connector 150 which is disposed on a proximal side of the outer tube 120 and which is configured to accommodate the inner shaft 130, and a hub 160 disposed on a proximal side of the inner shaft 130. In accordance with an exemplary embodiment, the image diagnosis catheter 100 according to the present embodiment is a rapid exchange (RX) type having a structure in which a guide wire passes through only a distal portion of the image diagnosis catheter 100.

In the description herein, a side inserted into the body cavity in the image diagnosis catheter 100 is referred to as a distal end or a distal side, the hub 160 side disposed in the image diagnosis catheter 100 is referred to as a proximal end or a proximal side, and an extending direction of the sheath 110 is referred to as an axial direction.

As illustrated in FIG. 2A, the drive shaft 140 passes through the sheath 110, the outer tube 120 connected to the proximal end of the sheath 110, and the inner shaft 130 inserted into the outer tube 120, and extends to the inside of the hub 160.

The hub 160, the inner shaft 130, the drive shaft 140, and the vibrator unit 145 are connected to each other so as to respectively and integrally move forward and backward in the axial direction. Therefore, for example, if an operation of pushing the hub 160 toward the distal side is performed, the inner shaft 130 connected to the hub 160 is pushed into the outer tube 120 and into the unit connector 150, thereby causing the drive shaft 140 and the vibrator unit 145 to move to the distal side inside the sheath 110. For example, if an operation of pulling the hub 160 to the proximal side is performed, the inner shaft 130 is drawn from the outer tube 120 and the unit connector 150 as indicated by an arrow a1 in FIGS. 1 and 2B. The drive shaft 140 and the vibrator unit 145 move to the proximal side inside the sheath 110 as indicated by an arrow a2.

As illustrated in FIG. 2A, when the inner shaft 130 is pushed most to the distal side, the distal portion of the inner shaft 130 reaches the vicinity of a relay connector 170. In this case, the vibrator unit 145 is located in the vicinity of the distal end of the sheath 110. The relay connector 170 serves as a connector for connecting the sheath 110 and the outer tube 120 to each other.

As illustrated in FIG. 2B, a slippage preventing connector 131 is disposed in the distal end of the inner shaft 130. The slippage preventing connector 131 has a function of preventing the inner shaft 130 from slipping out of the outer tube 120. When the hub 160 is pulled most to the proximal side, that is, when the inner shaft 130 is pulled out most from the outer tube 120 and the unit connector 150, the slippage preventing connector 131 is configured to be caught on a predetermined position on an inner wall of the unit connector 150.

In accordance with an exemplary embodiment, a communicating hole (not illustrated) which allows the inside and the outside of the sheath 110 to communicate with each other is disposed in the sheath 110. The communicating hole is a priming solution discharge hole for discharging a priming solution. When the image diagnosis catheter 100 is used, a priming process is performed to fill the sheath 110 with the priming solution in order to efficiently transmit and receive ultrasound by reducing ultrasound attenuation caused by air inside the sheath 110. When the priming process is performed, the priming solution can be discharged outward from the communicating hole, and gas such as the air can be discharged from the inside of the sheath 110 together with the priming solution.

As illustrated in FIGS. 2A and 2B, the hub 160 has direction confirming projections 163a and 163b used to confirm a direction of the hub 160 when a port 162 and the motor drive device 410 are connected to each other, and a connector unit 165 internally equipped with an electrode terminal which is mechanically and electrically connected to the motor drive device 410.

The X-ray imaging apparatus 200 is used to see through and image the subject P laid on the laying table 300 so as to support surgery. As illustrated in FIG. 1, the X-ray imaging apparatus 200 has an X-ray tube device 210, an X-ray image receiving device 220, a C-arm 230, and an alignment mechanism 240.

The X-ray tube device 210 is disposed at a predetermined distance away from the X-ray image receiving device 220 so as to face the X-ray image receiving device 220. The X-ray tube device 210 emits X-rays to the X-ray image receiving device 220.

The X-ray image receiving device 220 receives the X-rays emitted from the X-ray tube device 210, and displays a captured image of the subject P on the display unit 600.

In accordance with an exemplary embodiment, the C-arm 230 has a substantially C-shape, and both ends of the C-arm 230 support each of the X-ray tube device 210 and the X-ray image receiving device 220.

The alignment mechanism 240 rotates the C-arm 230 around the axis in the Z-direction, and moves the C-arm 230 on an XY plane, thereby moving the C-arm 230 to various imaging positions. Accordingly, the X-ray tube device 210 and the X-ray image receiving device 220 can be aligned with the imaging positions of the subject P. As illustrated in FIG. 1, the alignment mechanism 240 has a first rotary unit 241, a main body portion 242, and the rail unit 243.

In accordance with an exemplary embodiment, the first rotary unit 241 rotates the C-arm 230 around the axis in the Z-direction in a state where the first rotary unit 241 grips the C-arm 230. In addition, in a state of being supported by the main body portion 242, the first rotary unit 241 is configured to be slidable in the Y-direction along the cavity 242a disposed so as to extend to the main body portion 242 in the Y-direction.

The lower surface of the main body portion 242 has the cavity 242a formed so as to extend in the Y-direction. In a state of being supported by the rail unit 243, the main body portion 242 is configured to be slidable in the X-direction.

The rail unit 243 supports the main body portion 242. The rail unit 243 can be fixed to a ceiling (not illustrated).

The subject P is laid on the laying table 300. In accordance with an exemplary embodiment, the width of the laying table 300 along the width direction of the subject P is configured to be smaller than the distance at which the X-ray tube device 210 and the X-ray image receiving device 220 are separated from each other so that the X-ray tube device 210 and the X-ray image receiving device 220 can pass through the laying table 300.

The height of the laying table 300 in the Z-direction can be adjusted by a height adjustment mechanism 310. Means for adjusting the height of the laying table 300 by the height adjustment mechanism 310 is not particularly limited. However, for example, an electric hydraulic type may be used.

The medical device 400 supports the motor drive device 410 in a state where the motor drive device 410 is separated from the laying table 300 in the Z-direction. In addition, the medical device 400 moves the motor drive device 410 in XYZ-directions, and rotates the motor drive device 410 around the axis in the Z-direction.

As illustrated in FIG. 1, the medical device 400 has the motor drive device 410, a support unit 420, a drive unit 430, a first vibration resistance member 440, and a second vibration resistance member 450.

The motor drive device 410 is connected to the connector unit 165 (corresponding to the proximal end of the image diagnosis catheter) of the hub 160, thereby rotating the drive shaft 140 in the axial direction and moving the drive shaft 140 along the axial direction.

As illustrated in FIGS. 1 and 3, the motor drive device 410 has a scanner device 411 internally equipped with an external drive source such as a motor, and a movement device 412 which grips and moves the scanner device 411 in the axial direction by using motor.

As illustrated in FIG. 3, the scanner device 411 transmits and receives a signal to and from the vibrator unit 145 by being connected to the connector unit 165 of the hub 160, and transmits a driving force for rotating the drive shaft 140.

As illustrated in FIG. 3, the movement device 412 has a scanner gripping portion 412a for gripping and fixing the scanner device 411, and a catheter support unit 412b for supporting the image diagnosis catheter 100 so as not to be misaligned when moved.

As illustrated in FIG. 1, it can be preferable that the scanner device 411 is disposed so as to have the same height as that of the movement device 412 in the Z-direction. For example, in a case where the scanner device 411 is disposed above the movement device 412 in the Z-direction, there is a possibility that the scanner device 411 may interfere with the support unit 420. In addition, in a case where the scanner device 411 is disposed below the movement device 412 in the Z-direction, there is a possibility that the scanner device 411 may interfere with the second vibration resistance member 450. In contrast, the scanner device 411 according to the present embodiment is disposed parallel to the movement device 412 along the Y-direction. Accordingly, the scanner device 411 can be prevented from interfering with the support unit 420 and the second vibration resistance member 450. A configuration in which the above-described scanner device 411 is disposed above and below to the movement device 412 in the Z-direction is also included in the present disclosure.

Scanning using the ultrasound in the image diagnosis catheter 100 according to the present embodiment transmits the rotary movement of the motor inside the scanner device 411 to the drive shaft 140, and rotates the vibrator unit 145 fixed to the distal end of the drive shaft 140, thereby operating an image transmitted and received by the vibrator unit 145 in a substantially radial direction. In accordance with an exemplary embodiment, the whole image diagnosis catheter 100 is pulled to the hand-side, and the vibrator unit 145 is moved in the axial direction. In this manner, a tomographic image of 360° in the enclosing tissue body over the axial direction inside the blood vessel can be obtained in such a manner that any desired position can be scanned.

As illustrated in FIG. 1, the support unit 420 supports the motor drive device 410 in a state where the motor drive device 410 is separated from the laying table 300 in the Z-direction. In accordance with an exemplary embodiment, the support unit 420 supports the motor drive device 410 in a suspended state.

In accordance with an exemplary embodiment, the support unit 420 is a flexible arm. Here, for example, the flexible arm means a rod-shaped body, which can freely change a shape of the rod-shaped body by applying an external force, and can hold a changed shape. For example, a multi-joint arm can be employed. In the present embodiment, it can be preferable that the support unit 420 can hold the shape against the external force applied to an extent that the operator unintentionally collides with the support unit 420. According to this configuration, the posture or the position of the motor drive device 410 can be adjusted by adjusting the attitude or the position of the support unit 420 configured to include a flexible arm. Therefore, the position or the posture of the distal end of the image diagnosis catheter 100 can be finely adjusted during the procedure, thereby achieving a conveniently improved procedure.

In accordance with an exemplary embodiment, one end 421 of the support unit 420 interlocks with the motor drive device 410, and the support unit 420 extends upward from the one end 421 in the Z-direction. The other end 422 of the support unit 420 interlocks with the first vibration resistance member 440.

As illustrated in FIG. 1, the drive unit 430 has a second rotary unit (corresponding to a rotary unit) 431 which rotates the motor drive device 410 around the axis in the Z-direction, and a movement unit 432 which moves the motor drive device 410 on the XY-plane.

In accordance with an exemplary embodiment, the second rotary unit 431 rotates the motor drive device 410 around the axis in the Z-direction by rotating the support unit 420 around the axis in the Z-direction. The second rotary unit 431 can be fixed to an upper portion of the first vibration resistance member 440.

The movement unit 432 moves the motor drive device 410 on the XY-plane by moving the support unit 420 on the XY-plane. As illustrated in FIG. 1, the movement unit 432 has a Y-movement unit 433 and an X-movement unit 434.

In a state where the Y-movement unit 433 is supported by the X-movement unit 434, the Y-movement unit 433 is configured to be slidable in the Y-direction along the cavity 434a disposed so as to extend to the X-movement unit 434 in the Y-direction. The Y-movement unit 433 is disposed in an upper portion of the second rotary unit 431.

A lower surface of the X-movement unit 434 has the cavity 434a formed along the Y-direction. In a state where the X-movement unit 434 is supported by the rail unit 243, the X-movement unit 434 is configured to be slidable in the X-direction. The X-movement unit 434 is disposed in an upper portion of the Y-movement unit 433.

The first vibration resistance member 440 restrains vibrations generated by the motor drive device 410 rotationally operating the drive shaft 140. For example, in accordance with an exemplary embodiment, the first vibration resistance member 440 is a rubber member.

Similarly to the first vibration resistance member 440, the second vibration resistance member 450 restrains the vibrations generated by the motor drive device 410 rotationally operating the drive shaft 140. As illustrated in FIG. 1, the second vibration resistance member 450 is disposed on an upper surface of the laying table 300 in an arch shape so as to cross one leg of the subject P. Both end portions of the second vibration resistance member 450 are configured to be attachable to and detachable from the laying table 300. In addition, the second vibration resistance member 450 is configured to be attachable to and detachable from the movement device 412. The above-described attachment method is not particularly limited. However, for example, bolt fastening may be used.

For example, in a case where the first vibration resistance member 440 and the second vibration resistance member 450 are not provided, due to the vibrations generated by the motor drive device 410 rotationally operating the drive shaft 140 and heartbeats of the subject P, an image acquired by the image diagnosis catheter 100 may be disturbed. In contrast, according to the present embodiment, the first vibration resistance member 440 and the second vibration resistance member 450 are provided. Accordingly, the vibration generated by the motor drive device 410 rotationally operating the drive shaft 140 can be restrained. Therefore, the image acquired by the image diagnosis catheter 100 can be restrained (or prevented) from being disturbed. The above-described configuration in which the first vibration resistance member 440 and the second vibration resistance member 450 are not provided is also included in the present disclosure. In this case, the other end 422 of the support unit 420 interlocks with the second rotary unit 431.

In addition, for example, in a case where the second vibration resistance member 450 is not provided, in a procedure (to be described later), when the image diagnosis catheter 100 is inserted into the living body again after the image diagnosis catheter 100 is inserted into and then removed from the inside of the living body, it can be difficult to insert the image diagnosis catheter 100 into the living body again through a location into which the image diagnosis catheter 100 is initially inserted. In contrast, according to the present embodiment, when the image diagnosis catheter 100 is inserted into the living body again after the image diagnosis catheter 100 is inserted into the living body and then removed from the inside of the living body, the movement device 412 of the motor drive device 410 is attached to the second vibration resistance member 450. In this manner, the image diagnosis catheter 100 can be inserted into the living body again through the location into which the image diagnosis catheter 100 is initially inserted. That is, the second vibration resistance member 450 is provided, thereby achieving a conveniently improved procedure.

The control unit 500 controls various operations of the X-ray tube device 210, the alignment mechanism 240, the motor drive device 410, and the drive unit 430. In accordance with an exemplary embodiment, the control unit 500 can include a central processing unit (CPU) and a memory.

The display unit 600 is electrically connected to the control unit 500, and displays various images.

Next, a method of using the medical system 1 according to the present embodiment will be described with reference to FIGS. 1 to 4. In the following using method, the image diagnosis catheter 100 is inserted into the body cavity and is removed from the body cavity in such a way that the X-ray imaging apparatus 200 sees through and images the subject P.

First, in a state where the hub 160 is pulled most to the proximal side (refer to FIG. 2B), an operator connects a syringe (not illustrated) containing a priming solution to the port 162, pushes a plunger of the syringe, thereby injecting the priming solution into the sheath 110.

If the priming solution is injected into the sheath 110, the priming solution is released outward from the sheath 110 via the communicating hole, and gas such as air together with the priming solution is discharged outward from the inside of the sheath 110 (priming process).

After the priming process is performed, as illustrated in FIG. 3, the motor drive device 410 is connected to the connector unit 165 of the image diagnosis catheter 100. Then, the operator pushes the hub 160 until the hub 160 is attached to the proximal end of the unit connector 150, and moves the vibrator unit 145 to the distal side. In this state, the image diagnosis catheter 100 is inserted into a desired position inside the body cavity (for example, a blood vessel) along a guide wire (not illustrated) while the guide wire is inserted.

When the image diagnosis catheter 100 is inserted into the desired position inside the body cavity, the operator first operates the drive unit 430 so as to adjust a position in the XY-directions of the motor drive device 410 and an orientation around the axis in the Z-direction. In this manner, the position and the orientation are roughly adjusted so that the distal end of the image diagnosis catheter 100 is located in the vicinity of a target position inside the body cavity. Then, the operator adjusts a posture or a position of the support unit 420 configured to include a flexible arm. In this manner, the posture or the position is finely adjusted so that the distal end of the image diagnosis catheter 100 is located at the target position inside the body cavity, and the image diagnosis catheter 100 is inserted into the body cavity. That is, according to the medical device 400 of the present embodiment, a space formed above the laying table 300 can be effectively utilized for the target position inside the body cavity. In this manner, the image diagnosis catheter 100 is three-dimensionally accessible to the target position. As described above, in the image diagnosis catheter 100, the posture or the position of the drive unit 430 and the support unit 420 can be appropriately adjusted in accordance with a situation of the subject P or a situation of the procedure by operating the drive unit 430 and the support unit 420. Therefore, a conveniently improved procedure can be achieved.

In this case, in a state of being separated from the laying table 300 in the Z-direction, the motor drive device 410 is supported by the support unit 420. Accordingly, a space formed above the laying table 300 is effectively utilized. Therefore, it is possible to more freely design a position for placing the motor drive device 410.

When a tomographic image is obtained at the target position inside the body cavity, the vibrator unit 145 moves the drive shaft 140 to the proximal side while rotating together with the drive shaft 140 (pull-back operation). In this case, the vibrator unit 145 transmits and receives ultrasound.

The rotation and movement operation of the drive shaft 140 is controlled by the control unit 500. The connector unit 165 disposed inside the hub 160 is rotated in a state of being connected to the motor drive device 410, and the drive shaft 140 is rotated in conjunction therewith. The rotational speed of the connector unit 165 and the drive shaft 140 can be 1, 800 rpm, for example. Here, as described above, the medical device 400 according to the present embodiment has the first vibration resistance member 440 and the second vibration resistance member 450. Therefore, the vibrations generated by the motor drive device 410 rotationally operating the drive shaft 140 can be restrained (or prevented), and the image acquired by the image diagnosis catheter 100 can be restrained (or prevented) from being disturbed.

In addition, based on a signal transmitted from the control unit 500, the vibrator unit 145 transmits ultrasound into the body. The signal received by the vibrator unit 145 and corresponding to reflected waves is transmitted to the control unit 500 via the drive shaft 140 and the motor drive device 410. The control unit 500 generates the tomographic image of the body cavity, based on the signal transmitted from the vibrator unit 145, and displays a generated image on the display unit 600.

After the tomographic image of the body cavity is generated, the image diagnosis catheter 100 is removed from inside of the body cavity.

When the image diagnosis catheter 100 is removed from the inside of the body cavity, the operator adjusts the position or the posture of the support unit 420 configured to include a flexible arm. In this manner, the image diagnosis catheter 100 is removed from the inside of the body cavity. Then, after the image diagnosis catheter 100 is removed from inside of the body cavity, the operator operates the drive unit 430 so as to move a bending portion 423 of the support unit 420 in a direction away from the operator, as illustrated in FIG. 4 (upward to the right in FIG. 4). This operation can help prevent the procedure from being hindered by the presence of the support unit 420, thereby achieving a conveniently improved procedure.

Next, the operator inserts a balloon catheter (not illustrated) having a stent on an outer periphery thereof into the body cavity, and locates the stent at a stenosed site existing inside the body cavity.

Next, the operator inserts the image diagnosis catheter 100 into the body cavity again in order to confirm whether the stent is properly located in the stenosed site. In this case, the movement device 412 of the motor drive device 410 is attached to the second vibration resistance member 450. In this manner, the image diagnosis catheter 100 can be relatively easily inserted through the location into which the image diagnosis catheter 100 is initially inserted.

As described above, the medical device 400 according to the present embodiment has the motor drive device 410 that is connected to the connector unit 165 of the image diagnosis catheter 100, that rotates the drive shaft 140 around the axial direction, and that moves the drive shaft 140 along the axial direction, and the support unit 420 that supports the motor drive device 410 in a state where the motor drive device 410 is separated from the laying table 300 on which the subject P is laid in the Z-direction.

According to the medical device 400 configured in this way, the support unit 420 supports the motor drive device 410 in a state where the motor drive device 410 is separated from the laying table 300. Therefore, it is possible to more freely design a position for placing the motor drive device 410.

In addition, for example, when an atherectomy device serving as a device for cutting and removing the stenosed site in the blood vessel is used together in addition to the image diagnosis catheter 100, a drive device of the atherectomy device needs to be placed on the laying table 300. In this case, in a case where the motor drive device 410 is placed on the laying table 300, there can be a conflict between the drive device of the atherectomy device and the location of the motor drive device 410, or a cable becomes entangled in each drive device. In contrast, according to the medical device 400 of the present embodiment, the support unit 420 supports the motor drive device 410 in the state where the motor drive device 410 is separated from the laying table 300. Therefore, the conflict between the drive device of the atherectomy device and the location of the motor drive device 410 can be prevented, and/or the cable can be prevented from becoming entangled in each drive device.

In addition, the medical device 400 further has the second rotary unit 431 which rotates the motor drive device 410 around the axis in the Z-direction axis, and the movement unit 432 which moves the motor drive device 410 on the XY-plane orthogonal to the Z-direction. For example, in a case where the motor drive device 410 is placed at a lateral position of the leg of the subject P or a position between both the legs on the laying table 300, the position for placing the motor drive device 410 may not be optimal as an insertion target position inside the body cavity. In contrast, according to the configuration including the second rotary unit 431 and the movement unit 432, the motor drive device 410 can be moved to a suitable position, thereby achieving a conveniently improved procedure.

In addition, the support unit 420 is a flexible arm, which can freely change a shape thereof by applying an external force, and can hold a changed shape. According to this configuration, the posture or the position of the motor drive device 410 can be adjusted by adjusting the posture or the position of the support unit 420 configured to include the flexible arm. Therefore, the position or the posture of the distal end of the image diagnosis catheter 100 can be finely adjusted during the procedure, thereby achieving a conveniently improved procedure.

In addition, one end 421 of the support unit 420 interlocks with the motor drive device 410, and the support unit 420 extends upward from the one end 421 in the Z-direction. According to this configuration, the support unit 420 is not located between the motor drive device 410 and the laying table 300. Therefore, the procedure can be prevented from being hindered, thereby achieving a conveniently improved procedure.

In addition, the medical device 400 further has the first vibration resistance member 440 and the second vibration resistance member 450 for restraining the vibrations generated by the motor drive device 410 rotationally operating the drive shaft 140. Therefore, the vibrations generated by the motor drive device 410 rotationally operating the drive shaft 140 can be restrained, and the image acquired by the image diagnosis catheter 100 can be restrained from being disturbed.

Figure 5:
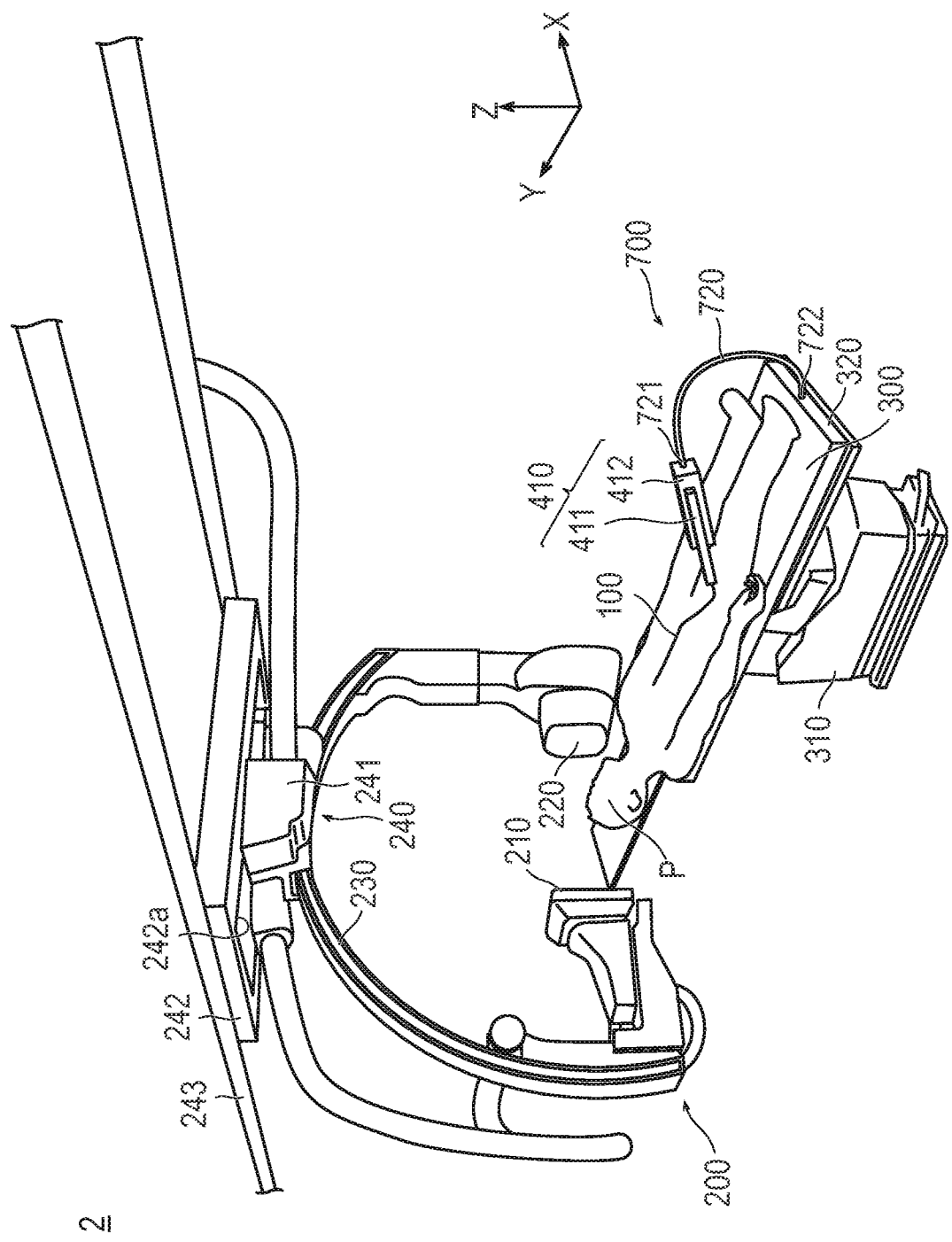
FIG. 5 is a perspective view illustrating a medical system according to a second embodiment.
Figure 6:
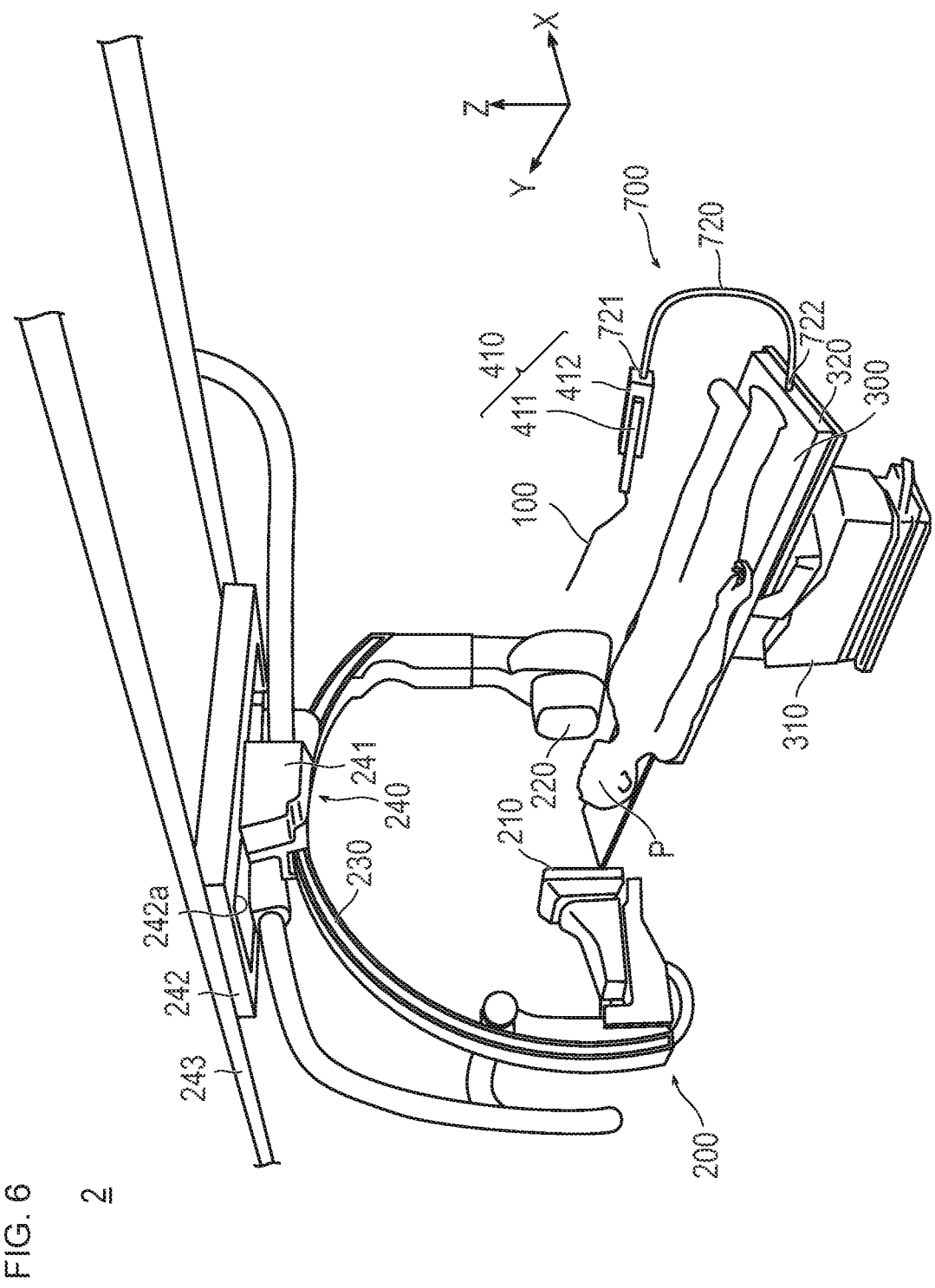
FIG. 6 is a view for describing a method of using the medical system according to the second embodiment.

Next, a second embodiment according to the present disclosure will be described with reference to FIGS. 5 and 6. FIG. 5 is a perspective view illustrating a medical system 2 according to the second embodiment. FIG. 6 is a diagram for describing a method of using the medical system 2 according to the second embodiment. Description will be omitted with regard to elements common to those in the first embodiment, and characteristic elements only in the second embodiment will be described. The same reference numerals will be given to members, which are the same as those according to the above-described first embodiment, and repeated description will be omitted. Compared to the first embodiment, the second embodiment has a different position with which the other end 722 of a support unit 720 interlocks.

As illustrated in FIG. 5, the medical system 2 according to the second embodiment has a medical device 700. Other configurations are the same as those according to the first embodiment, and thus, description thereof will be omitted.

As illustrated in FIG. 5, the medical device 700 has the motor drive device 410 and the support unit 720. The motor drive device 410 is the same as that according to the first embodiment, and thus, description thereof will be omitted.

As illustrated in FIG. 5, the support unit 720 supports the motor drive device 410 in a state where the motor drive device 410 is separated from the laying table 300 in the Z-direction.

In accordance with an exemplary embodiment, the support unit 720 is a flexible arm.

One end 721 of the support unit 720 interlocks with the motor drive device 410, and the support unit 720 extends downward from the one end 721 in the Z-direction. In the support unit 720, the other end 722 interlocks with a side surface 320 on the leg side of the subject P in the laying table 300. The support unit 720 may interlock with a side surface other than side surface 320 on the leg side of the subject P in the laying table 300.

Next, a method of using the medical system 2 according to this embodiment will be described with reference to FIGS. 5 and 6. The method of using the medical system 2 according to the second embodiment is different from the method of using the medical system 1 according to the first embodiment in a method of inserting the image diagnosis catheter 100 into the target position inside the body cavity and a method of remove the image diagnosis catheter 100 from the inside of the body cavity. Accordingly, the method of inserting the image diagnosis catheter 100 into the body cavity and the method of removing the image diagnosis catheter 100 from the inside of the body cavity will be described.

When the image diagnosis catheter 100 is inserted into the target position inside the body cavity, the operator adjusts the posture or the position of the support unit 720 configured to include the flexible arm. In this manner, the distal end of the image diagnosis catheter 100 is adjusted so as to be located at the target position inside the body cavity, and then, the image diagnosis catheter 100 is inserted into the body cavity. That is, according to the medical device 700 in the present embodiment, the image diagnosis catheter 100 is three-dimensionally accessible to the target position inside the body cavity.

In addition, when the image diagnosis catheter 100 is removed from the inside of the body cavity, the operator adjusts the position or the posture of the support unit 720 configured to include the flexible arm. In this manner, the image diagnosis catheter 100 is removed from the inside of the body cavity (refer to FIG. 6).

As described above, in the medical device 700 according to the second embodiment, one end 721 of the support unit 720 interlocks with the motor drive device 410, the support unit 720 extends downward from the one end 721 in the Z-direction, and the other end 722 interlocks with the laying table 300. According to this configuration, the support unit 720 is not located above the motor drive device 410. Therefore, the procedure can be prevented from being hindered, thereby achieving a conveniently improved procedure.

Figure 7:
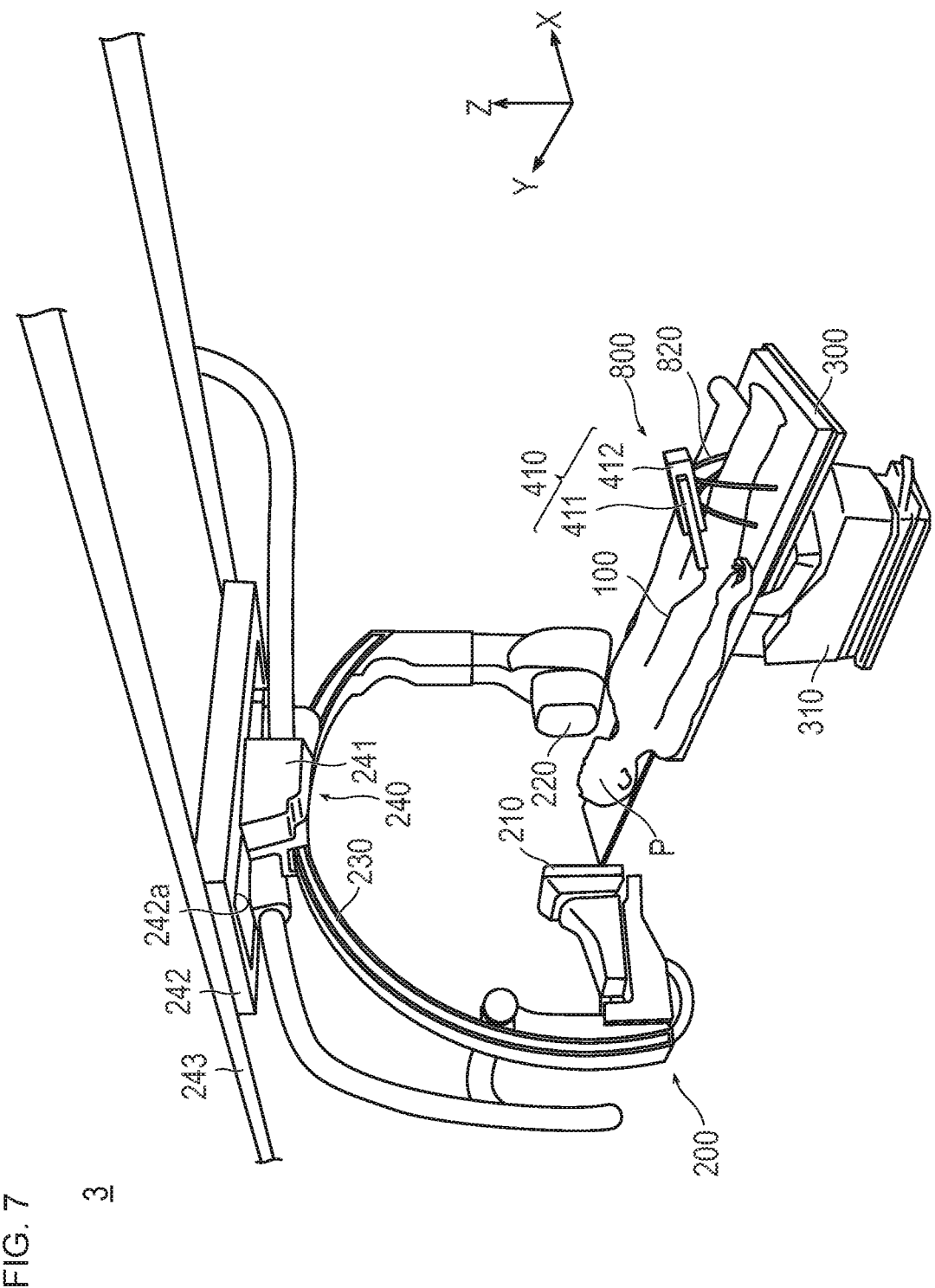
FIG. 7 is a perspective view illustrating a medical system according to a third embodiment.

Next, a third embodiment according to the present disclosure will be described with reference to FIG. 7. FIG. 7 is a perspective view illustrating a medical system 3 according to the third embodiment. Description will be omitted with regard to elements common to those in the second embodiment, and characteristic elements only in the third embodiment will be described. The same reference numerals will be given to members, which are the same as those according to the above-described second embodiment, and repeated description will be omitted. Compared to the second embodiment, the third embodiment has a different configuration of a support unit 820.

As illustrated in FIG. 7, the medical system 3 according to the third embodiment has a medical device 800. Other configurations are the same as those according to the second embodiment, and thus, description thereof will be omitted.

As illustrated in FIG. 7, the medical device 800 has the motor drive device 410 and the support unit 820. The motor drive device 410 is the same as that according to the first embodiment, and thus, description thereof will be omitted.

As illustrated in FIG. 7, the support unit 820 supports the motor drive device 410 in a state where the motor drive device 410 is separated from the laying table 300 in the Z-direction.

The support unit 820 is a flexible arm. According to the present embodiment, the image diagnosis catheter 100 is inserted into the body cavity, and the image diagnosis catheter 100 is removed from the inside of the body cavity by adjusting the posture or the position of the support unit 820 serving as the flexible arm.

The support unit 820 is disposed in a fan shape on the upper surface of the laying table 300 so as to cross one leg of the subject P. Both end portions of the support unit 820 can be configured to be attachable to and detachable from the laying table 300. In addition, the support unit 820 can be configured to be attachable to and detachable from the movement device 412.

As described above, according to the medical device 800 of the third embodiment, the support unit 820 having a simple configuration can support the motor drive device 410 in a state where the motor drive device 410 is separated from the laying table 300 in the Z-direction. Therefore, it is possible to more freely design the position for placing the motor drive device 410 while the configuration is restrained from becoming complicated.

Figure 8:
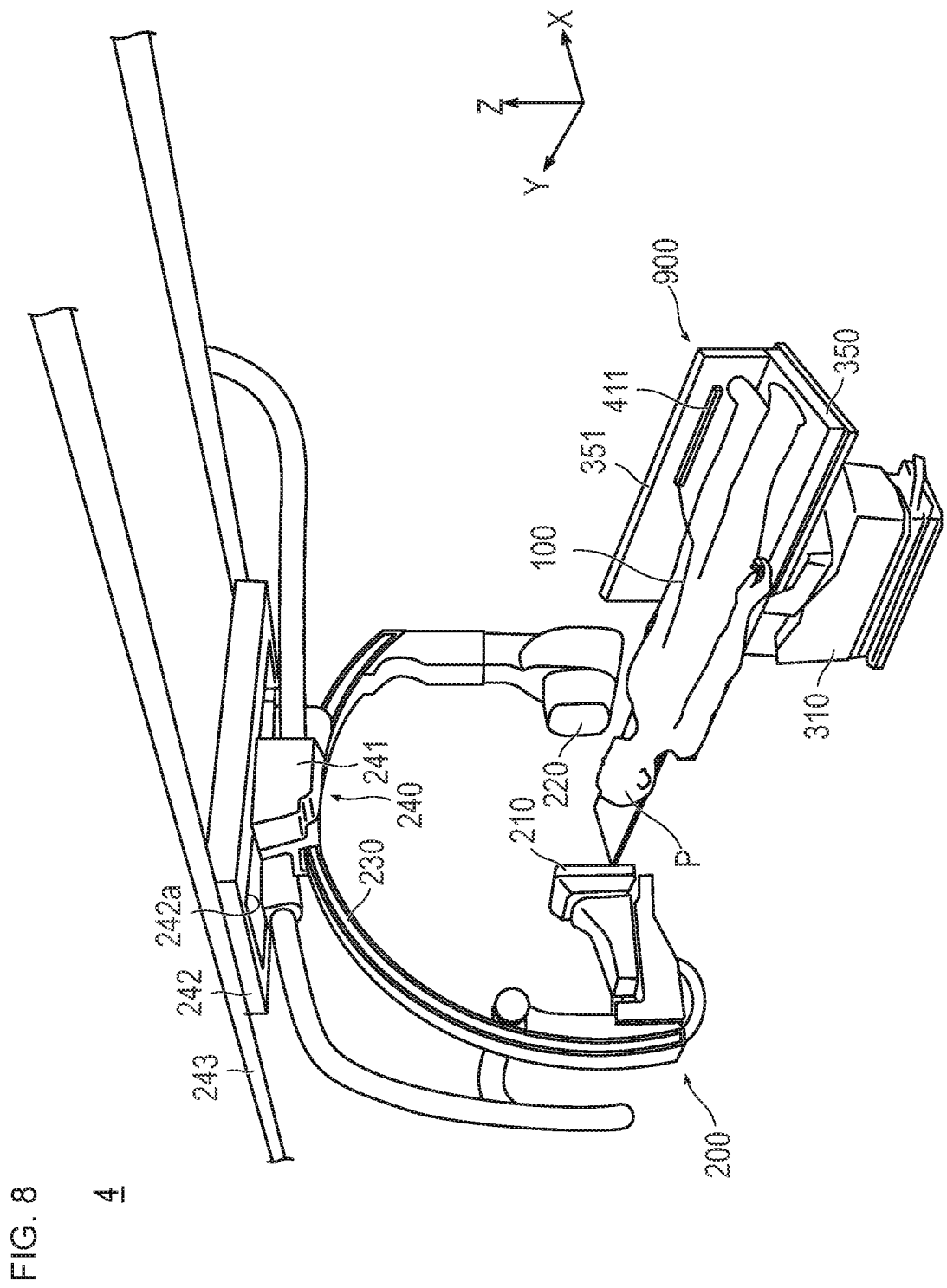
FIG. 8 is a perspective view illustrating a medical system according to a fourth embodiment.

Next, a fourth embodiment according to the present disclosure will be described with reference to FIG. 8. FIG. 8 is a perspective view illustrating a medical system 4 according to the fourth embodiment. Description will be omitted with regard to elements common to those in the first embodiment, and characteristic elements only in the fourth embodiment will be described. The same reference numerals will be given to members, which are the same as those according to the above-described first embodiment, and repeated description will be omitted. Compared to the first embodiment, the fourth embodiment has a different location for placing the scanner device 411.

The laying table 350 of the medical system 4 according to the fourth embodiment has a longitudinal wall 351 extending upward from a side surface located on the left side of the subject P in the Z-direction.

In the present embodiment, the longitudinal wall 351 functions as a support unit which supports the scanner device 411 in a state where the scanner device 411 is separated from the laying table 350 in the Z-direction. In addition, the longitudinal wall 351 also functions as a movement device, which grips the scanner device 411 and causes a motor to move the scanner device 411 in the axial direction.

As described above, according to the medical device 900 in the fourth embodiment, the longitudinal wall 351 functions as the support unit and the movement device. Therefore, according to a simple configuration, it is possible to more freely design the position for placing the motor drive device 410.

Hitherto, the image diagnosis catheter according to the present disclosure has been described with reference to the embodiments and modification examples. However, the present disclosure is not limited only to the configurations described in the embodiments and the modification examples. Based on the description in claims, the present disclosure can be appropriately changed.

For example, in the above-described first embodiment, the support unit 420 is the flexible arm. However, instead of the flexible arm, the support unit 420 may be a rigid body, which is not deformed.

In addition, in the above-described first embodiment, the motor drive device 410 is supported by the support unit 420 configured to include the flexible arm in a state where the motor drive device 410 is separated from the laying table 300 in the Z-direction. However, the support unit is not particularly limited as long as the support unit is configured to support the motor drive device 410 in a state where the motor drive device 410 is separated from the laying table 300 in the Z-direction. For example, the support unit may be an unmanned aerial vehicle capable of autonomous flying.

In addition, in the above-described first embodiment, the medical device 400 has the first vibration resistance member 440 and the second vibration resistance member 450. However, the medical device 400 may have any one of the first vibration resistance member 440 and the second vibration resistance member 450. In addition, the medical device 400 may not have the first vibration resistance member 440 and the second vibration resistance member 450.

In addition, in the above-described first embodiment, the scanner device 411 is disposed parallel to the movement device 412 along the Y-direction. However, a location where the scanner device 411 is disposed for the movement device 412 is not particularly limited. In addition, the scanner device 411 may be configured to be rotatable around the outer periphery of the movement device 412. According to this configuration, depending on the situation of the procedure, the position of the scanner device 411 for the movement device 412 can be adjusted, thereby achieving a conveniently improved procedure.

In addition, the image diagnosis catheter 100 according to the above-described embodiments is a rapid exchange type. However, the image diagnosis catheter 100 may be an over-the-wire type in which the guide wire extends from the distal end to the proximal end of the image diagnosis catheter 100.

In addition, in the above-described embodiments, the image diagnosis catheter used for intra vascular ultra sound (IVUS) as an application target of the image diagnosis catheter according to the present disclosure has been described as an example. However, for example, the present disclosure is also applicable to an image diagnosis catheter used for optical coherence tomography (OCT) or a hybrid-type (dual type) image diagnosis catheter which can be used for both the intra vascular ultra sound and the optical coherence tomography.

In addition, in the above-described first embodiment, the medical device 400 is used together with the X-ray imaging apparatus 200. However, the medical device 400 is not limited thereto as long as the medical device 400 is used for an examination in a state where the subject P is laid on the laying table 300. For example, the medical device 400 can be used together with an MRI examination apparatus or a CT examination apparatus.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
a motor drive device that is connected to a proximal end of an image diagnostic catheter, and configured to rotate a drive shaft inserted into the image diagnostic catheter around an axial direction and move the drive shaft along the axial direction; and
a support unit configured to support the motor drive device in a state where the motor drive device is separated in a Z-direction from a table on which a subject is laid;
wherein the support unit is a flexible arm configured to be bendable in a direction perpendicular to a longitudinal direction of the flexible arm by applying an external force and configured to hold a shape of the flexible arm in a bent state; and
wherein one end of the support unit in the longitudinal direction of the support unit interlocks with the motor drive device, and an other end of the support unit interlocks with a drive unit connected to a rail unit configured to be fixed to a ceiling, the drive unit comprising:
a first vibration resistance member configured to receive the other end of the support unit;
a rotary unit configured to rotate the motor drive device and the support unit around an axis in the Z-direction; and
a movement unit configured to move the motor drive device on a plane orthogonal to the Z-direction, and wherein the rotary unit is located between the first vibration resistance member and the movement unit.

2. The medical device according to claim 1, further comprising:
a second resistance member configured to prevent vibrations generated by the motor drive device rotationally operating the drive shaft.

3. The medical device according to claim 2, wherein the first vibration resistance member is a rubber member configured to receive the other end of the support unit and the second vibration resistance member configured to be attached on an upper surface of the table to restrain the vibrations generated by the motor drive device rotationally operating the drive shaft and to be disposed on the upper surface of the table in an arch shape and configured to cross over only one leg of the subject.

4. The medical device according to claim 1, wherein the support unit is a rigid body, which is not deformable.

5. The medical device according to claim 1, further comprising:
an X-ray imaging apparatus.

6. The medical device according to claim 1, wherein the motor drive device comprises:
a scanner device internally equipped with a motor; and
a movement device configured to move the scanner device in the axial direction.

7. A medical device comprising:
a motor connected to a proximal end of an image diagnostic catheter, and configured to rotate a drive shaft inserted into the image diagnostic catheter around an axial direction and move the drive shaft along the axial direction;
a support configured to support the motor in a state where the motor is separated in a Z-direction from a table on which a subject is laid; and
an arch shaped vibration resistance member configured to be attached on an upper surface of the table to restrain vibrations generated by the motor, the arch shaped vibration resistance member configured to cross over only one leg of the subject;
wherein the support is a flexible arm configured to freely change a shape of the flexible arm by applying an external force and configured to hold a changed shape;
wherein one end of the support interlocks with the motor, and an other end of the support interlocks with a drive unit connected to a rail unit configured to be fixed to a ceiling; and
the drive unit comprising:
  a vibration resistance member configured to receive the other end of the support unit;
  a rotary unit configured to rotate the motor drive device and the support unit around an axis in the Z-direction; and
  a movement unit configured to move the motor drive device on a plane orthogonal to the Z-direction, and wherein the rotary unit is located between the vibration resistance member and the movement unit.

8. A method of acquiring a diagnostic image, the method comprising:
inserting an image diagnostic catheter into a blood vessel of a subject on a table;
arranging a distal end of the image diagnostic catheter at a target position inside the blood vessel;
connecting a motor drive device to a proximal end of the image diagnostic catheter, the motor drive device configured to rotate a drive shaft included in the image diagnostic catheter around an axial direction and move the drive shaft along the axial direction;
arranging a support unit configured to support the motor drive device in a state where the motor drive device is separated in a Z-direction from the table on which the subject is laid;
applying an external force to the support unit to bend the support unit in a direction perpendicular to a longitudinal direction of the support unit, the support unit being a flexible arm configured to hold a shape of the flexible arm in a bent state; and
interlocking one end of the support unit in the longitudinal direction of the support unit with the motor drive device, and interlocking an other end of the support unit with a drive unit connected to a rail unit fixed to a ceiling, the drive unit comprising a first vibration resistance member that receives the other end of the support unit, a rotary unit configured to rotate the motor drive unit and support unit around an axis in the Z-direction, and a movement unit configured to move the motor drive device on a plane orthogonal to the Z-direction, the rotary unit being located between the first vibration resistance member and the movement unit.

9. The method according to claim 8, comprising:
obtaining a tomographic image at the target position inside the blood vessel with the image diagnostic catheter.

10. The method according to claim 8, comprising:
obtaining an x-ray image at the target position with an x-ray imaging apparatus.

11. The medical device according to claim 1, wherein the rotary unit is fixed to an upper surface of the first vibration resistance member.

12. The medical device according to claim 1, wherein the movement unit includes an X-movement unit and Y-movement unit, the X-movement unit configured to move the movement unit along an X-direction and the Y-movement unit configured to move the movement unit along a Y-direction, and wherein the X-movement unit is supported by the rail unit, and Y-movement unit is disposed in an upper cavity of the rotary unit.

13. The medical device according to claim 3, wherein the second vibration resistance member is configured to be attachable and detachable from the table.

14. The medical device according to claim 6, further comprising:
a second vibration resistance member is configured to be attachable and detachable to the movement device of the motor drive device.

15. The medical device according to claim 5, wherein the X-ray imaging apparatus includes an X-ray tube device configured to emit X-rays, an X-ray image receiving device configured to receive the X-rays emitted from the X-ray tube device, a C-arm, and an alignment mechanism, the C-arm configured to support the X-ray tube device and the X-ray receiving device, and the alignment mechanism configured to rotate the C-arm around an axis in the Z-direction and move the C-arm on an XY plane.

16. The medical device according to claim 7, wherein the second vibration resistance member is configured to be attachable and detachable from the table.

17. The medical device according to claim 7, wherein the motor drive device comprises:
a scanner device internally equipped with a motor; and
a movement device configured to move the scanner device in the axial direction.

18. The medical device according to claim 17, further comprising:
a second vibration resistance member is configured to be attachable and detachable to the movement device of the motor drive device.

19. The method according to claim 8, further comprising:
attaching a second vibration resistance member to the motor drive device and placing the second vibration resistance member on an upper surface of the table, the second vibration resistance member having an arch shape and configured to cross over only one leg of the subject.

* * * * *